(12) United States Patent
Jacobine et al.

(10) Patent No.: US 10,414,845 B2
(45) Date of Patent: Sep. 17, 2019

(54) PROCESS FOR PREPARING HIGH MOLECULAR WEIGHT POLYACRYLATES HAVING NARROW POLYDISPERSITY INDICES AND COMPOSITIONS MADE THEREFROM

(71) Applicant: Henkel IP & Holding GmbH, Duesseldorf (DE)

(72) Inventors: Anthony F. Jacobine, North Haverhill, NH (US); John G. Woods, Farmington, CT (US); David P. Dworak, Middletown, CT (US); Darel Gustafson, Shelton, CT (US)

(73) Assignee: Henkel IP & Holding GmbH, Duesseldorf (DE)

( * ) Notice: Subject to any disclaimer, the term of this patent is extended or adjusted under 35 U.S.C. 154(b) by 0 days.

(21) Appl. No.: 15/638,468

(22) Filed: Jun. 30, 2017

(65) Prior Publication Data
US 2017/0298162 A1 Oct. 19, 2017

Related U.S. Application Data

(63) Continuation of application No. PCT/US2015/059648, filed on Nov. 9, 2015.

(60) Provisional application No. 62/101,207, filed on Jan. 8, 2015.

(51) Int. Cl.
| | | |
|---|---|---|
| *C08F 220/18* | (2006.01) | |
| *C08F 220/26* | (2006.01) | |
| *C08F 8/26* | (2006.01) | |
| *C08F 8/34* | (2006.01) | |
| *C08F 220/06* | (2006.01) | |
| *C07C 31/20* | (2006.01) | |
| *C07C 321/02* | (2006.01) | |
| *C08F 220/14* | (2006.01) | |
| *C08F 297/02* | (2006.01) | |
| *C08G 81/02* | (2006.01) | |
| *C08F 2/38* | (2006.01) | |

(52) U.S. Cl.
CPC ............ *C08F 220/06* (2013.01); *C07C 31/20* (2013.01); *C07C 321/02* (2013.01); *C08F 2/38* (2013.01); *C08F 220/14* (2013.01); *C08F 297/023* (2013.01); *C08G 81/021* (2013.01); *C08F 220/18* (2013.01); *C08F 2438/01* (2013.01); *C08F 2500/01* (2013.01); *C08F 2500/03* (2013.01)

(58) Field of Classification Search
CPC .. C08F 8/26; C08F 8/34; C08F 220/18; C08F 220/26; C08F 2220/1808; C08F 2220/1825; C08F 2220/281; C08K 5/0025; C08K 5/053; C08K 5/092; C08K 5/37; C08J 3/24

See application file for complete search history.

(56) References Cited

U.S. PATENT DOCUMENTS

| | | | |
|---|---|---|---|
| 6,111,022 A | 8/2000 | Matyjaszewski et al. | |
| 6,538,091 B1 * | 3/2003 | Matyjaszewski | C08F 4/00 526/328 |
| 6,838,535 B2 | 1/2005 | Percec | |
| 8,450,427 B2 | 5/2013 | Percec | |
| 2007/0004874 A1 * | 1/2007 | Kitano | C08G 8/10 525/524 |
| 2009/0275707 A1 | 11/2009 | Balk et al. | |
| 2010/0010178 A1 * | 1/2010 | Balk | C08F 4/00 526/95 |
| 2013/0018122 A1 * | 1/2013 | Woods | C07C 323/52 522/35 |

FOREIGN PATENT DOCUMENTS

| | | |
|---|---|---|
| EP | 0789036 | 8/1997 |
| WO | 1996030421 | 10/1996 |
| WO | 2009117654 | 9/2009 |
| WO | 2012012705 | 1/2012 |
| WO | 2013043573 | 3/2013 |
| WO | 2014149411 | 9/2014 |

OTHER PUBLICATIONS

International Search Report issued in connection with International Patent Application No. PCT/US2015/059648 dated Mar. 3, 2016.
Kato et al., "Polymerization of Methyl Methacrylate with the Carbon Tetrachloride/Dichlorotris-(triphenylphosphine)ruthenium(II)/Methylaluminum Bis(2,6-di-tert-butylphenoxide) Initiating System: Possibility of Living Radical Polymerization", Macromolecules, vol. 28, No. 5, pp. 1721-1723 (1995).

* cited by examiner

*Primary Examiner* — Vu A Nguyen
(74) *Attorney, Agent, or Firm* — Steven C. Bauman

(57) ABSTRACT

A method of preparing high molecular weight poly(meth)acrylate polymers having narrow polydispersity indices (PDIs) by coupling poly(meth)acrylate building block units which themselves have narrow PDIs. The building block units have halogenated terminations, which when reacted with selected coupling agents, from the high molecular weight poly(meth)acrylate polymers.

18 Claims, No Drawings

PROCESS FOR PREPARING HIGH MOLECULAR WEIGHT POLYACRYLATES HAVING NARROW POLYDISPERSITY INDICES AND COMPOSITIONS MADE THEREFROM

FIELD OF THE INVENTION

The invention relates generally to the preparation of high molecular weight polyacylate polymers having narrow polydispersity indices (PDI). These high molecular weight polymers are formed by coupling polyacrylate polymer units having narrow PDI's to form higher molecular weight polyacrylate polymers which have essentially the same PDI as the polyacrylate starting units.

BACKGROUND OF RELATED TECHNOLOGY

Controlled radical polymerization (CRP) methods, such as single electron transfer living radical polymerization (SET-LRP) and atom transfer radical polymerization (ATRP) have been used to form polyacrylate polymers having narrow PDIs. Currently, however, these CRP methods suffer from disadvantages associated with producing high molecular weight polyacrylates having low PDIs. In particular, during the CRP process, as the higher molecular weight species are generated they become insoluble in the solvent systems in which they are made. For example, at molecular weights of about 40,000 and greater insolubility becomes apparent processing difficulties such as high viscosities attendant the increased molecular weight occur. The viscosity can become so great as to make processing extremely difficult and not practical for commercialization. There is a need for a method, for making high molecular weight polyacrylates having narrow PDIs which do not suffer from such insolubility and viscosity issues and which allow for practical and commercially viable methods.

SUMMARY OF THE INVENTION

The invention relates to a process for preparing high molecular weight poly(meth)acrylate polymers having narrow PIDs by reacting terminally-halogenated poly(meth)acrylate 'building-block" units having narrow PDIs with a coupling reagent to link the building block units together and form a higher molecular weight polymer, while maintaining or substantially maintaining the PDI of the original building blocks.

Thus, in one aspect of the invention there is provided a process for preparing high molecular weight poly(meth)acrylates with narrow polydispersity indices (PDI) which include the steps of:
 a. providing a solution of terminally-halogenated poly(meth)acrylate units having a PDI of about 1.01 to about 3.0, desirably about 1.4 or less;
 b. reacting the solution with a coupling reagent selected from the group consisting of a diacid, a diol, a dithiol and mixtures thereof for a time and at a temperature sufficient to permit said terminally-halogenated poly(meth)acrylate units to be coupled together via the coupling reagent to form a higher molecular weight poly(meth)acrylate polymer as compared to the individual terminally-halogenated poly(meth)acrylate units (building blocks). The PDI of the final coupled polymer is about 1.01 to about 3.0, desirably 1.4 or less.

In another aspect of the invention there is provided a polymer comprising at least two poly(meth)acrylate units (building blocks) coupled together via a linkage selected from the group consisting of an ester linkage, an ether linkage and a thiol ether linkage, wherein the average molecular weight (Mw) of the coupled polymer is about 30,000 to about 360,000, preferably about 40,000 to about 160,000, and more preferably 60,000 to about 100,000.

In another aspect of the invention there is provided a poly(meth)acrylate polymer having the structure: A-B-C, wherein each of A, B and C are poly(meth)crylate units (building blocks) which may be the same or different and wherein B and C are linked to A via a linkage, the linkage being selected from an ester linkage, an ether linkage and a thiol ether linkage and wherein the average molecular weight (Mw) of the poly(meth)acrylate polymer is 30,000 to about 250,000, preferably about 40,000 to about 160,000, and more preferably 60,000 to about 100,000.

In yet another aspect of the invention there is provided a high molecular weight poly(meth)acrylate polymer formed from the reaction of terminally-halogenated poly(meth)acrylate units having a narrow PDI and a coupling reagent selected from the group consisting of diacids, diols and dithiols.

DETAILED DESCRIPTION OF THE INVENTION

For purposes of this invention, the terms (meth)acrylate(s) or poly(meth)acrylate(s) are intended to include methacrylates and acrylates, and polymethacrylates and polyacrylates, respectively. All amounts are in percent weight unless otherwise specified.

The present invention provides novel high molecular weight polyacrylate polymer (HMWPAP) structures having narrow PDIs, as well as novel methods of making such structures. Additionally, the present invention includes novel compositions made from HMWPAPs, including polymerizable compositions useful as adhesives, sealants and coatings. The compositions of the present invention have diverse applications in fields such as the electronic industry, automotive industry, consumer industry, building industry, aircraft industry and packaging industry, among others.

The novel HMWPAPs having narrow PDIs overcome the problems associated with known CRP methods for making high molecular weight polymers. By making relatively small polymer units having the desired PDI and coupling them together in the manner described herein to make HMWPAPs which maintain the narrow PDIs, the aforementioned processing problems are overcome. Additionally, using the coupling techniques of the present invention allows for unique tailoring of the end product, since a variety of different types of units may be coupled together to provide desired end products and properties, providing flexibility in both processing and end-product not currently available in known CRP methods.

The poly(meth)acrylate building block units of the present invention have a narrow PDI ranging from about 1.4 to about 3.0, desirably from about 1.2 to about 1.8, and more desirably from about 1.01 to about 1.2. PDIs of about 1.4 or less are most desirable. The narrow PDIs are desirably carried through into the assembled HMWPAPs. The building blocks desirably are made using a CRP process, and most desirably an SET-LRP process, as described in PCT/US2011/044992, PCT/US2014/018187 and PCT/US2012/055870, each of which are herein incorporated by reference in their entirety. When the building blocks are made using a SET-LRP process, such building blocks will desirably be made by charging a reactor system with a polymerizable reaction fluid comprising at least one polymerizable (meth) acrylate monomer, at least one solvent for said monomer, a metal salt, at least one ligand, at least one initiator and a catalyst. The reaction is run for a time and temperature sufficient to produce a desired level of polymer conversion having the desired polydispersity and average molecular weight. The average molecular weights (Mw) of the building block polymers may range from about 10,000 to about 120,000 and desirably about 30,000 to about 100,000 and more desirably about 40,000 to about 75,000.

Components for Preparing the Narrow PDI Polyacrylate Building Blocks

The building blocks of the HMWPAPs desirably made using CRP, and most desirably using SET-LRP processes, as described herein.

Useful (meth)acrylate monomers for making the building blocks include, without limitation, difunctional and monofunctional monomers. Specific monofunctional examples include: (meth)acrylic acid, methyl(meth)acrylate, ethyl (meth)acrylate, n-propyl (meth)acrylate, isopropyl (meth) acrylate, n-butyl (meth)acrylate, isobutyl (meth)acrylate, tert-butyl (meth)acrylate, n-pentyl (meth)acrylate, n-hexyl (meth)acrylate, cyclohexyl (meth)acrylate, n-heptyl (meth) acrylate, n-octyl (meth)acrylate, 2-ethylhexyl (meth)acrylate, nonyl (meth)acrylate, decyl (meth)acrylate, dodecyl (meth)acrylate, phenyl (meth)acrylate, toluoyl (meth)acrylate, benzyl (meth)acrylate, 2-methoxyethyl (meth)acrylate, 3-methoxybutyl (meth)acrylate, 2-hydroxyethyl (meth)acrylate, 2-hydroxypropyl (meth)acrylate, stearyl (meth)acrylate, glycidyl (meth)acrylate, 2-aminoethyl (meth)acrylate, (methacryloyloxypropyl)trimethoxysilane, (meth)acrylic acid-ethylene oxide adduct, trifluoromethylmethyl (meth) acrylate, 2-trifluoromethylethyl (meth)acrylate, 2-perfluoroethylethyl (meth)acrylate, 2-perfluoroethyl-2-perfluorobutylethyl (meth)acrylate, 2-perfluoroethyl (meth)acrylate, perfluoromethyl (meth)acrylate, diperfluoromethylmethyl (meth)acrylate, 2-perfluoromethyl-2-perfluoroethylethyl (meth)acrylate, 2-perfluorohexylethyl (meth)acrylate, 2-perfluorodecylethyl (meth)acrylate, 2-perfluorohexadecylethyl (meth)acrylate and combinations thereof.

Non-limiting examples of difunctional (meth)acrylates for making the building blocks include: glycol dimethacrylate, diethylene glycol dimethacrylate, ethylene glycol dimethacrylate, polyethylene glycol dimethacrylate, butanediol dimethacrylate, hexanediol dimethacrylate, decanediol dimethacrylate, dodecanediol dimethacrylate, Bisphenol-A-dimethacrylate, trimethylol propane trimethacrylate, and mixtures thereof.

Useful, non-limiting solvents for making the building blocks include water, methanol, ethanol, propanol, isopropanol, butanol, and tert butanol, ethylene glycol, diethylene glycol, triethylene glycol, 2-(2-ethoxyethoxy)ethanol, tetraethylene glycol, glycerine, HEMA, a phenol, DMSO, DMF, DMAc, NMP, ethylene carbonate, and propylene carbonate, and combinations thereof. The amount of solvent in the reaction polymerization medium is in the range of about 5 to about 75 weight %, preferably in the range of about 5 to about 30 weight % based on the total weight of the polymerization medium.

Useful initiators for making the building blocks include, without limitation, compounds of the formula R—X or R'C(=O)OR" where X is a halogen, R is a $C_1$-$C_6$ alkyl substituted or unsubstituted, R' is a $C_1$-$C_6$ alkyl containing at least one halogen atom (e.g., 1, 2 or 3) attached to the carbon atom adjacent to the carbonyl group, and R" is a $C_1$-$C_6$ alkyl. For example, the initiator may include: diethyl meso-2,5-dibromoadipate; dimethyl 2,6-dibromoheptanedioate, ethylene glycol bis(2-bromopropionate); ethylene glycol mono-2-bromopropionate; trimethylolpropane tris(2-bromopropionate); pentaerythritol tetrakis (2-bromopropionate); 2,2-dichloacetophenone; methyl 2-bromopropionate; methyl 2-chloropropionate; N-chloro-2-pyrrolidinone; N-bromosuccinimide; polyethylene glycol bis(2-bromopropionate); polyethylene glycol mono(2-bromopropionate); 2-bromopropionitrile; dibromochloromethane; 2,2-dibromo-2-cyanoacetamide; α,α'-dibromo-ortho-xylene; α,α'-dibromo-meta-xylene; α,α'-dibromo-para-xylene; α,α'-dichloro-para-xylene; 2-bromopropionic acid; methyl trichloroacetate; para-toluenesulfonyl chloride; biphenyl-4,4'-disulfonyl chloride; diphenylether-4,4'-disulfonylchloride bromoform; iodoform carbon tetrachloride; and combinations thereof. In some embodiments, the initiator may be an alkyl, sulfonyl, or nitrogen halide. The nitrogen halide can also be halogenated nylon, peptide, or protein. Alternatively, in some embodiments, the initiator may be a polymer containing active halide groups, for example, poly(vinyl)chloride, polychrolomethylsytrene. Further initiators include hexahalogenated ethane, mono-di, and tri haloacetates, acetophenones, halogenated amides, and polyamides such as nylons, halogenated urethanes and polyurethane including their block copolymers, halogenated imides, acetone, and any other initiators shown to work with conventional metal catalyzed living radical polymerization including SET-LRP.

The catalyst for the polymerization of the building blocks is generally a complex of a metal or metal salt with a ligand. Suitable metals are transition metals such as, for example, Cu, Mn, Ni, Pt, Fe, Ru, V, Au, Ag, Hg, Rh, Co, Ir, Os, Re, Cr, Mo, W, Nb, Ta, Zn, and the like. Suitable salts of the above-noted metals are, for example, halides, acetates, oxides, sulfides and the like. A preferred metal is copper and a preferred salt is Cu(II) bromide. The metal catalyst may also be selected one or more of Cu(O), $Cu_2O$, $Cu_2S$, $Cu_2Se$, $Cu_2Te$. The catalyst added directly to the reaction fluid, or used as part of a surface of the reactor vessel or conduits used in the vessel, in which the polymerizable reaction fluid comes in contact during the reaction. Desirably, the catalyst surface is pre-treated with a reducing agent. The amount of catalyst used should be present in sufficient amounts to convert said polymerizable reaction fluid to a radical living polymer (RLP) having a polydispersity of about 1.01 to about 3.0, desirably about 1.2 to about 1.8 and more desirably about 1.01 to about 1.2. PDIs of less than about 1.4 are desirable.

The reaction fluid for forming the building blocks may also include a component selected from $CuBr_2$, $CuCl_2$ and combinations thereof.

Useful ligands used to make the building blocks include without limitation, nitrogen-containing ligands suitable to aid in the extraction of the metal (or metal salt) catalyst to the extent that the metal catalyst may be solubilized by the ligand and thus available in its higher oxidation state. Particularly useful ligands include materials selected from the group consisting of tris(2-dimethylaminoethyl)amine (Me6-TREN), tris(2-aminoethyl)amine (TREN), 2,2-bipyridine (BPY) and N,N,N,N,N-pentamethyldiethylenetriamine (PMDETA).

A general reaction scheme for preparing the building blocks by SET-LRP is depicted as follows:

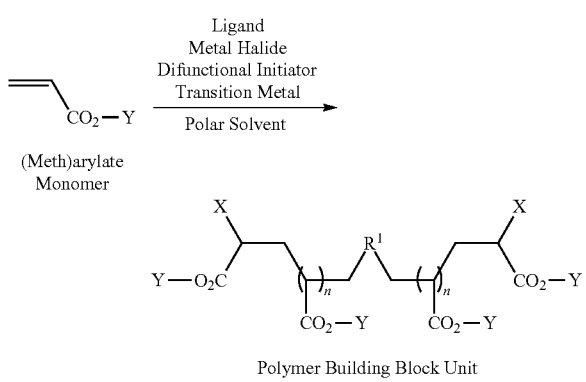

Wherein Y is alkyl $C_{1-20}$, $R^1$ is a hydrocarbyl group $C_{1-20}$ which may be interrupted by one or more heteroatoms and is substantially free of radically polymerizable groups, and which may contain one or more functional groups selected from the group consisting of hydroxyl, alkoxy, epoxy, ether, ester, amine, carbamate, amide and combinations thereof; and n is 10-10,000.

It is desirable to have a narrow molecular weight distribution, i.e., polydispersity index in the final polymer product. This is achieved by starting with narrow PDIs in the building blocks and coupling them together in a manner which preserves and imparts the narrow PDIs to the final coupled polymer structure. A narrow molecular weight distribution may be achieved from the polymerization in accordance with the present invention, as the chain length, end group functionality, and consistency of the polymer is substantially constant. In achieving a narrow molecular weight distribution, several factors may be managed. Some factors which contribute to a narrow molecular weight distribution include: (1) a rate of initiation that is competitive with the rate of propagation (allowing the simultaneous growth of all the polymer chains); (2) the exchange between species of different reactivity's being faster than propagation (ensuring that all the active chain termini are equally susceptible to reaction with monomer for a uniform growth); (3) low to no chain transfer or termination; (4) the rate of activation versus deactivation; and (5) a homogenous system where mixing is sufficiently fast (all active centers are introduced at the onset of the polymerization). A polymerization which meets these factors may have a polydispersity close to the theoretical value of the Poisson distribution 1+1/DP. For example, the PDIs of the polymer products of the present methods may be below 1.9, e.g. 1.1 to 1.4; more specifically less than 1.4, e.g. 1.1 to 1.2; and in certain cases less than 1.1, e.g. 1.035.

Coupling of the Building Blocks to Form High Molecular Weight Poly(Meth)Acrylates Having Narrow PDIs Once the poly(meth)acrylate building block units are formed, they must be coupled to form the high molecular weight poly(acrylate) polymers. The building block units are terminated with halogen groups such that they can be further reacted with the coupling reagent. Bromine is the preferred halogen, but other halogens such as chlorine and iodine and are also useful.

To form the halogen-terminated poly(meth)acrylate building blocks, one or more (meth)acrylates are reacted in the presence of an initiator such as those described herein (and including diethyl meso-2,5-dibromoadipate), a metal halide such as Cu(II)Br$_2$, a ligand such as the nitrogen-containing ligands described above (e.g., Me6-tren), a transition metal (e.g., Cu(O) and solvent (e.g. aprotic polar solvents, such as dimethylsulfoxide (DMSO)).

Once the halogen-terminated (meth)acrylate is formed, it is combined with the selected coupling agent (e.g. a diacid, a diol, and/or dithiol) under temperatures of about 40° C. to about 60° C. and permitted to react for a sufficient time to insure adequate coupling has occurred. The coupling reaction is generally run at temperatures from about room temperature (23° C.) to about 100° C., desirably at temperatures about 50° C. to about 70° C. The reaction time may vary but generally greater than 4 hours up to about 6 hours is sufficient. The resultant structure may be confirmed by chromatographic and spectroscopic analysis as shown in the examples.

The coupling agent may be a monofunctional or difunctional coupling agent. For example, a monofunctional coupling agent would have one end terminated with a carboxylic acid, thiol, or diol group and a difunctional coupling agent would have each of its ends terminated with a carboxylic acid, thiol, or diol group. For example, a difunctional coupling agent can be represented by: D-B-D where B is a substituted or substituted hydrocarbon chain $C_{1-20}$ and D would be a carboxylic acid, thiol, or diol group.

A monofunctional poly(meth)acrylate may also be coupled with itself to yield chemical structures which generally correspond to the following:

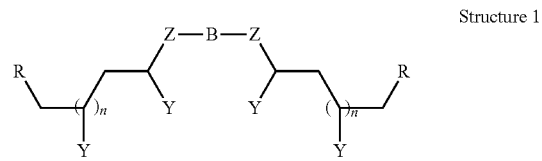

Structure 1

Wherein R is a monofuntional initiator fragment derived from halogenated compounds which initiate metal-catalyzed controlled radical polymerization;

N is 10-10,000

Y is alkyl $C_{1-20}$

Z is an ester, thiol, or ether linkage;

B is a substituted or unsubstituted hydrocarbon chain $C_{1-20}$, and

X is a halogen selected from Br, I and Cl. Among the useful monofuntional initiators (corresponding to R of Structure 1), include without limitation, Methyl 2-bromopropionate, Methyl 2-chloropropionate, Ethyl 2-bromopropionate, Ethyl 2-chloropropionate, 2-bromopropionic acid, 2-chloropropionic acid, 2-bromo-2-methylpropionic acid, and 2-bromobutyric acid.

A chemical structure for the coupling of a difunctional poly(meth)acrylate with itself maybe represented as follows:

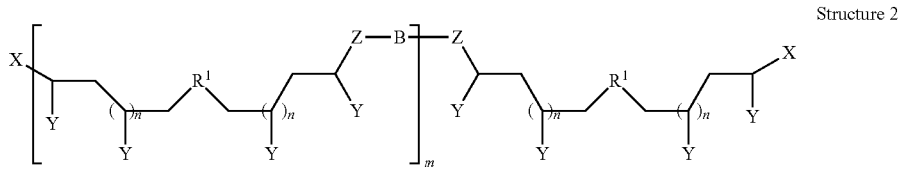

Where X, Y, Z, B and n are as defined in Structure 1 and $R^1$ is a hydrocarbon group $C_{1-20}$ which may be interrupted by one or more heteroatoms and is substantially free of radically polymerizable groups, and which may contain one or more functional groups selected from the group consisting of hydroxyl, alkoxy, epoxy, ether, ester, amine, carbamate, amide and combinations thereof; and m 1-10.

Of course, a difuntional poly(meth)acrylate building block may be coupled with another difunctional poly(meth)acrylate and a monfunctional (meth)acrylate.

EXAMPLES

Example 1

Coupling Br Functionalized Terpolymer with 4,4' Thiolbisbenzenethiol

To a 3-neck round bottle flask equipped with a Teflon stir blade and condenser was added 86.71 g (24,950 g/mol, 0.00695 moles Br) of terpolymer made from an SET-LRP process having a PID of 1.19 and heated to 55° C. by means of an oil bath. Dimethyl sulfoxide (DMSO) (about 100 mL) was added while the reaction flask was heating. The terpolymer has made from 75% butyl acrylate, 20% ethyl acrylate and 5% methoxy ethyl acrylate. The preparation of the terpolymer was in accordance with the following reaction scheme:

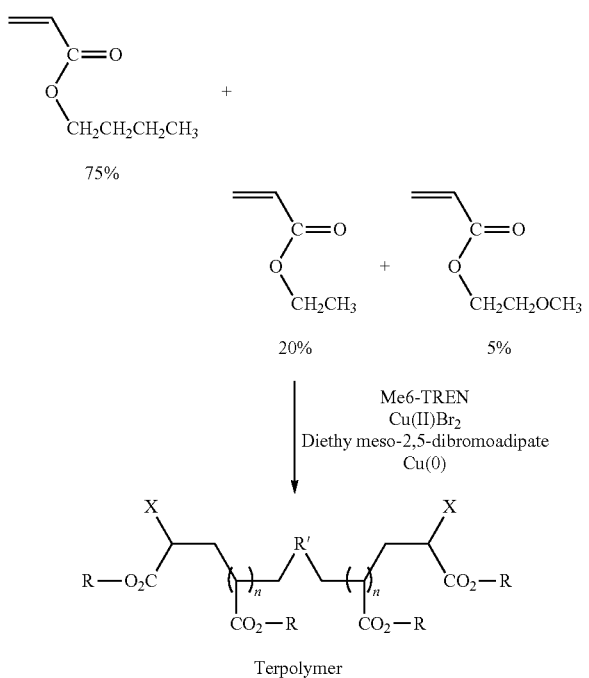

Terpolymer wherein R is alkyl $C_{1-4}$;
n is 10-500;
X is Br;
and R' is

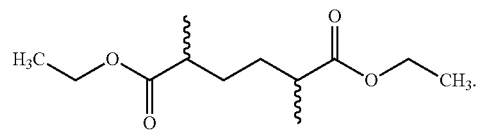

Once the terpolymer solution was at 55° C., it was stirred and potassium carbonate (0.64 g, 0.00452 moles) was added and allowed to mix. 4,4'-thiolbisbenzenethiol (0.565 g, 0.00452 moles) was then added and the flask was sealed with a glass stopper. The solution was allowed to react for over 4 hours at 55° C. When finished the solution was diluted with about 500 mL of toluene and mixed. The solution was washed twice with brine and the organic layer was isolated and dried over magnesium sulfate. The solution was then pressure filtered through a 0.5 micron filter and the solution was concentrated by means of rotovap (60° C., about 500 mTorr, over 5 hrs). The result was a viscous yellow polymer.

The structure of the polymer was confirmed by chromatographic and spectroscopic analysis. Size exclusion chromatography (DEC; THF; 1 mL/min; RI detector; PMMA calibtration) indicated number average molecular weight (Mn) of 37,775 and a polydispersity of 2.01. Residual bromide by x-ray fluorescence showed 3,447 ppm Br, which corresponds to approximately 46% of the bromine being reacted. Proton NMR (300 MHz) also confirmed the presence of the benzylic protons from 4,4'-thiolbisbensenethiol which has been coupled to the terpolymer chains.

Example 2

Coupling Br Functionalized Terpolymer with 1,4-Butanediol Bis(Thioglycolate)

To a 3-neck round bottom flask equipped with a Teflon Stir blade and condenser was added 96.088 g/mol, 0.00597 moles Br) of the same terpolymer used in Example 1 (but having a PDI 1.14) and heated to 60° C. by means of an oil bath. DMSO (about 30 mL) was added while the reaction was flask was heating. Once the terpolymer solution was at 60° C. it was stirred and potassium carbonate (0.495 g, 0.00358 moles) was added and allowed to mix. 1,4-butanediol bis(glycolate) (0.427 g, 0.00358 moles) was then added and the flask was sealed with a glass stopper. The solution was allowed to react for over 4 hours at 60° C. When finished the solution was diluted with about 500 mL of toluene and mixed. The solution was then washed twice with brine and the organic layer was isolated and dried over magnesium sulfate. The solution was then pressure filtered through a 0.5 micron filter and the solution was concentrated by means of a rotovap (60° C., about 500 mTorr, over 5 hours). The result was a viscous yellow polymer.

The structure of the polymer was confirmed by chromatographic and spectrographic analyses. Size exclusion chromatography (SEC: THF, 1 mL/min; RI detector; PMMA calibration) indicated number average molecular weight (Mn) of 41,426 and a polydispersity of 1.69. Residual bromide by x-ray fluorescence showed 2,783 ppm Br, which corresponds to approximately 45% of the bromine being reacted.

Example 3

Coupling Br Functionalized Terpolymer with Terephthalic Acid

To a 3-neck round bottom flask equipped with a Teflon blade and condenser was added 136.58 g (32.086 g/mol, 0.00851 moles Br) of the same terpolymer as Example 2 and heated to 70° C. by means of an oil bath. DMSO (about 50 mL) was added while the reaction flask was heating. Once the terpolymer solution was at 60° C. it was stirred and potassium carbonate (0.0352 g, 0.00244 moles) was added and allowed to mix. Terephthalic acid (0.0424 g, 0.0051 moles was then added and the flask was sealed with a glass stopper. The solution was allowed to react for over 12 hours at 70° C. When finished the solution was diluted with about 600 mL of toluene and mixed. The solution was then washed twice brine and the organic layer was isolated and dried over magnesium sulfate. The solution was then pressure filtered through a 0.5 micron filter and the solution was concentrated by means of a rotovap (60° C., about 500 mTorr, over 5 hours). The result was a viscous yellow polymer.

The structure of the polymer was confirmed by chromatographic and spectrographic analysis. Size exclusion chromatography (SEC: THF, 1 mL/min; RI detector: PMMA calibration) indicated number average molecular weight (Mn) of 31,513 and polydispersity of 1,23. Residual bromide by x-ray fluorescence showed 3,200 ppm Br, which corresponds to approximately 36% of the bromine being reacted.

Example 4

UV Polymerizable Composition Formed Using the Polymers Formed by the Present Invention A coupled poly(butyl acrylate) polymer is formed by the present invention and 55.5% by weight of this polymer is combined with 17.5% by weight N.N-dimethylacrylamide, 14% silica filler, 5% by weight isodecyl acrylate, 5% by weight PEG 400 ester (plasticizer), 1% by weight Vulcanox ZMB-2/c5 (mercaptobenzimidazole accelerator), 1% by weight Irganox B215 (antioxidant) and 1% Irgacure 2022 (photoinitiator) This composition is then subjected to uv light and cured rapidly.

Example 5

Moisture Curable Composition Using Polymers Formed by the Present Invention

The coupled polymer of Example 4 is used but this time with alkoxy group substitutions having been incorporated into the polymer to make the polymer curable using a moisture cure mechanism. The composition includes 83.67% by weight coupled poly(butyl acrylate) polymer, 6% by weight Plasticizer (alky sulfonic ester of phenol); 4.19% silica filler; 1.66 vinyltrimethoxy silane crosslinker, 2.08% by weight aminopropyltrimethoxysilane crosslinker, and 2.08% dibutyltin dilaurate catalyst. The composition is cured under ambient exposure to moisture.

The invention claimed is:

1. A process for preparing high molecular weight poly(meth)acrylates with narrow polydispersity indices (PDI) comprising the steps of:
    a. providing a solution of poly(meth)acrylate units having at least one terminal halogen atom and having a PDI of about 1.01 to about 3.0; and
    b. reacting the solution with a coupling reagent for a time and at a temperature sufficient to permit said terminally-halogenated poly(meth)acrylate units to be coupled together via the coupling reagent to form a high molecular weight poly(meth)acrylate polymer having a molecular weight (Mw) of greater than about 60,000 and a PDI of about 1.01 to about 3.0, wherein the terminally-halogenated poly(meth)acrylate units include a poly(meth)acrylate backbone formed from ethyl (meth)acrylate, butyl(meth)acrylates, and 2-methoxyethyl (meth)acrylate.

2. The process of claim 1, wherein the coupling reagent is a diacid selected from the group consisting of ethanedioic acid, propanedioic acid, butanedioic acid, pentanedioic acid, hexanedioic acid, heptanedioic acid, octanedioic acid, nonanedioic acid, decanedioic acid, undecanedioic acid, dodecanedioic acid, benzene-1,2-dicarboxylic acid, benzene-1,3-dicarboxylic acid, benzene-1,4-dicarboxylic acid, 2-(2-carboxyphenyl)benzoic acid, (Z)-butenedioic acid, (E)-butenedioic acid, pent-2-enedioic acid, dodec-2-enedioic acid, (2E, 4E)-hexa-2,4-dienedioic acid and combinations thereof.

3. The process of claim 1, wherein the coupling reagent is a diol selected from the group consisting of 1,2-butanediol, 1,3-butanediol, 1,4-butanediol, 2,3-butanediol, 1,4-butynediol, cyclohexane-1,2-diol, cyclohexanedimethanol, diethylene glycol, dipropylene glycol, ethylene glycol, glycerol, 1,6-hexanediol, 2-methyl-2,4-pentanediol, neopentyl glycol, 1,5-pentanediol, propylene glycol, 2,2,4,4-tetramethyl-1,3-cyclobutanediol, triethylene glycol and combinations thereof.

4. The process of claim 1, wherein the coupling reagent is a dithiol selected from the group consisting of 1,2-ethanedithiol, 1,3-propanedithiol, 1,4-butanedithiol, 2,3-butanedithiol, 1,5-pentanedithiol, benzene-1,4-dithiol, 2,2'-(ethylenedioxy)diethanethiol, 1,6-hexanedithiol, tetra(ethylene glycol) dithiol, 1,8-octanedithiol, 1,9-nonanedithiol, 1,11-undecanedithiol, 5,5'-bis(mercaptomethyl)-2,2'-bipyridine, hexa(ethylene glycol) dithiol, 1,16-hexadecanedithiol, 4,4'-thiolbisbenzenethiol and combinations thereof.

5. The process of claim 1, wherein the PDI of the high molecular weight polymer is about 1.01 to about 1.4.

6. The process of claim 1, wherein the time of said reacting is about 3 to about 6 hours.

7. The process of claim 1, wherein the temperature of said reacting is about room temperature (23° C.) to about 100° C.

8. The process of claim 1, wherein the terminally-halogenated poly(meth)acrylate units include a halogen selected from the group consisting of bromine, chlorine, iodine and mixtures thereof.

9. A polymer comprising poly(meth)acrylate polymer units coupled together via a linkage selected from the group consisting of an ester linkage, ether linkage, and a thiol ether linkage, wherein the average molecular weight (Mw) of the polymer is greater than about 60,000 to about 250,000 and the polydispersity index is about 1.01 to about 1.4, wherein poly(meth)acrylate units include a poly(meth)acrylate backbone formed from ethyl (meth)acrylate, butyl(meth)acrylates, and 2-methoxyethyl (meth)acrylate.

10. A poly(meth)acrylate polymer having the structure:

B-A-C wherein A, B and C are poly(meth)acrylate polymer units which are the same or different from each other; and wherein B and C are each joined to A via a coupling linkage, and the poly(meth)acrylate polymer has an average molecular weight (Mw) of greater than about 60,000 to about 250,000 and a polydispersity index of about 1.01 to about 1.4, wherein poly(meth)acrylate units include a poly(meth)acrylate backbone formed from ethyl (meth)acrylate, butyl(meth)acrylates, and 2-methoxyethyl (meth)acrylate.

11. The poly(meth)acrylate polymer of claim 10, wherein A, B and C are formed from monomers selected from the group consisting of (meth)acrylic acid, methyl(meth)acrylate, ethyl (meth)acrylate, n-propyl (meth)acrylate, isopropyl (meth)acrylate, n-butyl (meth)acrylate, isobutyl (meth)acrylate, tert-butyl (meth)acrylate, n-pentyl (meth)acrylate, n-hexyl (meth)acrylate, cyclohexyl (meth)acrylate, n-heptyl (meth)acrylate, n-octyl (meth)acrylate, 2-ethylhexyl (meth)acrylate, nonyl (meth)acrylate, decyl (meth)acrylate, dodecyl (meth)acrylate, phenyl (meth)acrylate, toluoyl (meth)acrylate, benzyl (meth)acrylate, 2-methoxyethyl (meth)acrylate, 3-methoxybutyl (meth)acrylate, 2-hydroxyethyl (meth)acrylate, 2-hydroxypropyl (meth)acrylate, stearyl (meth)acrylate, glycidyl (meth)acrylate, 2-aminoethyl (meth)acrylate, (methacryloyloxypropyl)trimethoxysilane, (meth)acrylic acid-ethylene oxide adduct, trifluoromethylmethyl (meth)acrylate, 2-trifluoromethylethyl (meth)acrylate, 2-perfluoroethylethyl (meth)acrylate, 2-perfluoroethyl-2-perfluorobutylethyl (meth)acrylate, 2-perfluoroethyl (meth)acrylate, perfluoromethyl (meth)acrylate, diperfluoromethylmethyl (meth)acrylate, 2-perfluoromethyl-2-perfluoroethylethyl (meth)acrylate, 2-perfluorohexylethyl (meth)acrylate, 2-perfluorodecylethyl (meth)acrylate, 2-perfluorohexadecylethyl (meth)acrylate and combinations thereof.

12. The poly(meth)acrylate polymer of claim 10, wherein the coupling linkage joining each of B and C to A is formed from a diacid selected from the group consisting of ethanedioic acid, propanedioic acid, butanedioic acid, pentanedioic acid, hexanedioic acid, heptanedioic acid, octanedioic acid, nonanedioic acid, decanedioic acid, undecanedioic acid, dodecanedioic acid, benzene-1,2-dicarboxylic acid, benzene-1,3-dicarboxylic acid, benzene-1,4-dicarboxylic acid, 2-(2-carboxyphenyl)benzoic acid, (Z)-butenedioic acid, (E)-butenedioic acid, pent-2-enedioic acid, dodec-2-enedioic acid, (2E, 4E)-hexa-2,4-dienedioic acid and combinations thereof.

13. The poly(meth)acrylate polymer of claim 10, wherein the coupling linkage joining each of B and C to A is formed from a diol selected from the group consisting of 1,2-butanediol, 1,3-butanediol, 1,4-butanediol, 2,3-butanediol, 1,4-butynediol, cyclohexane-1,2-diol, cyclohexanedimethanol, diethylene glycol, dipropylene glycol, ethylene glycol, glycerol, 1,6-hexanediol, 2-methyl-2,4-pentanediol, neopentyl glycol, 1,5-pentanediol, propylene glycol, 2,2,4,4-tetramethyl-1,3-cyclobutanediol, triethylene glycol and combinations thereof.

14. The poly(meth)acrylate polymer of claim 10, wherein the coupling linkage joining each of B and C to A is formed from a dithiol selected from the group consisting of 1,2-ethanedithiol, 1,3-propanedithiol, 1,4-butanedithiol, 2,3-butanedithiol, 1,5-pentanedithiol, benzene-1,4-dithiol, 2,2'-(ethylenedioxy)diethanethiol, 1,6-hexanedithiol, tetra(ethylene glycol) dithiol, 1,8-octanedithiol, 1,9-nonanedithiol, 1,11-undecanedithiol, 5,5'-bis(mercaptomethyl)-2,2'-bipyridine, hexa(ethylene glycol) dithiol, 1,16-hexadecanedithiol, 4,4'-thiolbisbenzenethiol and combinations thereof.

15. The poly(meth)acrylate polymer of claim 10, further including terminal functional groups selected from the group consisting of carboxylic acid, hydroxyl, thiol, alkoxy, halogen and combinations thereof.

16. The poly(meth)acrylate polymer of claim 10, further including a polymerization cure system.

17. The poly(meth)acrylate polymer of claim 16, wherein the polymerization cure system is selected from a heat cure system, a uv cure system, a redox cure system, an anionic cure system and combinations thereof.

18. A poly(meth)acrylate polymer formed from the reaction of: terminally-halogenated poly(meth)acrylate units and a coupling reagent selected from the group consisting of diacids, diols, dithiols and combinations thereof, wherein the terminally-halogenated poly(meth)acrylate units include a poly(meth)acrylate backbone formed from ethyl (meth)acrylate, butyl(meth)acrylates, and 2-methoxyethyl (meth)acrylate, and wherein the poly(meth)acrylate polymer has an average molecular weight (Mw) of greater than about 60,000 to about 250,000 and a PDI of about 1.01 to about 1.4.

* * * * *